(12) United States Patent
Liphardt et al.

(10) Patent No.: US 7,307,724 B1
(45) Date of Patent: Dec. 11, 2007

(54) METHOD OF REDUCING THE EFFECT OF NOISE IN DETERMINING THE VALUE OF A DEPENDENT VARIABLE

(75) Inventors: Martin M. Liphardt, Lincoln, NE (US); Blaine D. Johs, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 748 days.

(21) Appl. No.: 10/794,204

(22) Filed: Mar. 5, 2004

Related U.S. Application Data

(63) Continuation-in-part of application No. 10/034,800, filed on Dec. 28, 2001, now Pat. No. 6,822,738, and a continuation-in-part of application No. 09/945,962, filed on Sep. 4, 2001, now Pat. No. 7,075,649, and a continuation-in-part of application No. 09/496,011, filed on Feb. 1, 2000, now Pat. No. 6,353,477, which is a continuation-in-part of application No. 09/246,888, filed on Feb. 8, 1999, now Pat. No. 6,084,675, which is a continuation-in-part of application No. 08/912,211, filed on Aug. 15, 1997, now Pat. No. 5,872,630, which is a continuation-in-part of application No. 08/530,892, filed on Sep. 20, 1995, now Pat. No. 5,666,201, and a continuation-in-part of application No. 08/618,820, filed on Mar. 20, 1996, now Pat. No. 5,706,212.

(60) Provisional application No. 60/473,618, filed on May 28, 2003, provisional application No. 60/452,675, filed on Mar. 10, 2003, provisional application No. 60/437,023, filed on Dec. 31, 2002, provisional application No. 60/427,043, filed on Nov. 18, 2002, provisional application No. 60/424,589, filed on Nov. 7, 2002.

(51) Int. Cl.
*G01J 4/00* (2006.01)
(52) U.S. Cl. ...................................................... 356/369
(58) Field of Classification Search ........ 356/364–369; 250/225
See application file for complete search history.

(56) References Cited

U.S. PATENT DOCUMENTS

| | | | | |
|---|---|---|---|---|
| 4,668,086 A | | 5/1987 | Redner | 356/33 |
| 5,091,320 A | * | 2/1992 | Aspnes et al. | 427/8 |
| 5,166,752 A | | 11/1992 | Spanier et al. | 356/369 |
| 5,298,972 A | * | 3/1994 | Heffner | 356/364 |
| 5,504,582 A | | 4/1996 | Johs et al. | 356/369 |
| 5,581,350 A | | 12/1996 | Chen et al. | 356/369 |
| 5,596,406 A | | 1/1997 | Rosencwaig et al. | 356/327 |

(Continued)

OTHER PUBLICATIONS

WO 01/90687 A2, Thernawave, Nov. 29, 2001.

(Continued)

*Primary Examiner*—Hoa Q. Pham
(74) *Attorney, Agent, or Firm*—James D. Welch

(57) ABSTRACT

A method of reducing the effect of systematic and/or random noise during determination of dependent variable values, (eg. pseudo "n" and "k" and/or ellipsometric PSI and DELTA or mathematical equivalent vs. wavelength or angle of incidence), involving selecting a mathematical function and an independent variable subset range combination so that a square error best fit with total summed square error over the independent variable subset range being minimized, zero or within an acceptable range near zero, are achieved.

22 Claims, 2 Drawing Sheets

U.S. PATENT DOCUMENTS

| | | | |
|---|---|---|---|
| 5,666,201 A | 9/1997 | Johs et al. | 356/369 |
| 5,706,212 A | 1/1998 | Thompson et al. | 364/525 |
| 5,757,494 A * | 5/1998 | Green et al. | 356/369 |
| 5,793,480 A | 8/1998 | Lacey et al. | 356/73 |
| 5,872,630 A | 2/1999 | Johs et al. | 356/369 |
| 5,877,859 A | 3/1999 | Aspnes et al. | 356/364 |
| 5,956,145 A * | 9/1999 | Green et al. | 356/364 |
| 5,973,787 A | 10/1999 | Aspnes et al. | 356/369 |
| 6,134,012 A | 10/2000 | Aspnes et al. | 356/369 |
| 6,320,657 B1 | 11/2001 | Aspnes et al. | 356/369 |

OTHER PUBLICATIONS

WO 01/086257 A3, Senetech, Nov. 15, 2001.
Regression Calibration Method for Rotating Element Ellipsometers, Thin Solid Films, Johs 234 (1993).
Systematic and Random Errors in Rotating-Analyzer Ellipsometry, Nijs, et al Opt. Soc. Am D. vol. 5, No. 6 (Jun. 1988).

* cited by examiner

METHOD OF REDUCING THE EFFECT OF NOISE IN DETERMINING THE VALUE OF A DEPENDENT VARIABLE

This application is a CIP of application Ser. No. 10/034,800 Filed Dec. 28, 2001 now U.S. Pat. No. 6,822,738 and therevia a CIP of Ser. No. 09/945,962 filed Sep. 4, 2001 now U.S. Pat. No. 7,075,649 and Ser. No. 09/496,011 filed Feb. 1, 2000 (U.S. Pat. No. 6,353,477), which is a CIP of Ser No. 09/246,888 filed Feb. 8, 1999 (U.S. Pat. No. 6,084,675), which is a CIP of Ser. No. 08/912,211 filed Aug. 15, 1997 (U.S. Pat. No. 5,872,630), which is a CIP Ser. No. 08/530,892 filed Sep. 20, 1995 (U.S. Pat. No. 5,666,201) and therevia is a CIP of Ser. No. 08/618,820 filed Mar. 20, 1996 (U.S. Pat. No. 5,706,212). This application also Claims Benefit of, either directly or via Utility Applications which previously preserved them, Provisional Application Ser. No. 60/452,675 Filed Mar. 10, 2003; 60/473,618, Filed May 28, 2003; 60/437,023 Filed Dec. 31, 2002; 60/424,589, Filed Nov. 7, 2002; and 60/427,043 Filed Nov. 18, 2002.

TECHNICAL FIELD

The disclosed invention relates to methods of determining the values of dependent variables, and more specifically to a method of evaluating dependent variables which can be represented as a function of an independent variable in a mathematical function, based upon data which contains noise.

BACKGROUND

It is known to cause electromagnetic radiation to interact with a sample to obtain data which determines Ellipsometric Parameters, as a function of wavelength and/or angle-of-incidence, and then to perform mathematical regression of a proposed mathematical model of said sample onto values for ellipsometric PSI and DELTA to obtain values of, for instance, thickness and optical constants, where said ellipsometric PSI and DELTA are identified by:

$$\rho = rp/rs = \text{Tan}(\Psi)\exp(i\Delta)$$

In most cases the regression procedure is successful in providing useful information without the need to pre-condition data to reduce the effects of noise therein. In some cases, however, where it is desired to determine such as a pseudo-"n" and/or pseudo-"k" value of a sample at a specific wavelength, the presence of noise can be a significant source of uncertainty. (Note, pseudo-"n" and pseudo-"k" refer to "n" and "K" for a sample investigated as a monolithic whole, without taking into account specific structure). The disclosed invention provides an approach to overcoming such data analysis difficulty without the need to develop an accurate mathematical model for a sample structure.

A Search for relevant patents, provided a patent to Johs et al., U.S. Pat. No. 5,872,630, from which the present Application is derived as a CIP via intervening CIP Applications. Said 630 patent primarily describes a spectroscopic rotating compensator material system investigation system. Amongst other disclosure said 630 patent describes a Mathematical Regression based Calibration procedure which makes possible the use of essentially any compensator regardless of non-achromatic characteristics. And specifically, parameterization of variables was disclosed as an approach to optimizing use of information available in a data set. The basic concept of the presently Claimed approach to minimizing the effects of noise in data, in the context of data obtained from the practice of ellipsometry, was established and disclosed in said 630 patent which was Filed Aug. 15, 1997.

Additional demonstrative patents which disclose use of a spectroscopic range of wavelengths were also identified as follows.

A patent to Johs, from which the 630 patent was Continued-in Part, is No. 5,666,201, filed Sep. 20, 1995. The focus in said 201 patent comprises a detector arrangement in which multiple orders of a dispersed beam of electromagnetic radiation are intercepted by multiple detector systems.

U.S. Pat. No. 5,706,212, Issued Jan. 6, 1998, and Filed Mar. 20, 1996 for an Infrared Ellipsometer System Regression based Calibration Procedure. Said 212 patent describes use of an Substantially Achromatic Rotating Compensator and application of Mathematical Regression in a Calibration procedure which evaluates calibration parameters in both rotating and stationary components. The 212 patent describes that $2\omega$MEGA and $4\omega$OMEGA associated terms are generated by a detector of a signal which passes through a compensator caused to rotate at a rate of OMEGA. Said 630 patent was Continued-in-Part therefrom, as is the present application via an intervening patent application.

A patent to Chen et al., U.S. Pat. No. 5,581,350 is identified as it describes the application of regression in calibration of ellipsometer systems similar to that described in a paper by Johs in 1993.

Other patents are identified as generally describing ellipsometry systems which contain means which can generate data containing systematic or random noise, to which the disclosed invention can be applied.

Patents to Aspnes et al. are Nos. 6,320,657 B1, 6,134,012, 5,973,787 and 5,877,859. These patents describe a Broadband Spectroscopic Rotating Compensator Ellipsometer System wherein the Utility is found in the use of a "substantially Non-Achromatic" compensator and selecting a Wavelength Range and Compensator so that "an effective phase retardation value is induced covering at least from 90 degrees to 180 degrees", (012 patent), over a range of wavelengths of at least 200-800 nm. The 787 and 859 recite that at least one wavelength in said wavelength Range has a retardation imposed of between 135 and 225 Degrees, and another wavelength in the wavelength Range has a retardation imposed which is outside that retardation Range.

A recently published PCT Application is No. WO 01/90687 A2, which is based on U.S. application Ser. No. 09/575,295 filed May 3, 2001. This application was filed by Thermawave Inc. and specifically describes separate use of a $2\omega$ and a $4\omega$ term to provide insight to sample thickness and temperature.

Two patents which identify systems which utilize Polychromatic light in investigation of material systems, U.S. Pat. Nos. 5,596,406 and 4,668,086 to Rosencwaig et al. and Redner, respectively, were also identified.

Also identified is a patent to Woollam et al, U.S. Pat. No. 5,373,359 as it describes a Rotating Analyzer Ellipsometer System which utilizes white light. Patents continued from the 359 Woollam et al. U.S. Pat. Nos. 5,504,582 to Johs et al. and 5,521,706 to Green et al. Said 582 Johs et al. and 706 Green et al. patents describe use of polychromatic light in a Rotating Analyzer Ellipsometer System.

As the disclosed invention contemplates use of focused and non-focused beams of electromagnetic radiation, patents which describe means for focusing in ellipsometer systems were also identified.

A PCT Patent Application, No. WO 01/086257 is also known and is disclosed as it describes a combination of an aperture and lens to define a spot on a sample.

A patent to Lacey et al., U.S. Pat. No. 5,793,480 is disclosed as it describes a field stop and lens combination in an ellipsometer prior to a sample.

A patent to Spanier et al., U.S. Pat. No. 5,166,752 is disclosed as it describes an ellipsometer with lenses and apertures before and after a sample.

Regarding Articles, an article by Johs, titled "Regression Calibration Method For Rotating Element Ellipsometers", which appeared in Thin Film Solids, Vol. 234 in 1993 is also identified as it predates the Chen et al. patent and describes an essentially similar approach to ellipsometer calibration.

A paper by de Nijs et al., titled "Systematic and Random Errors in Rotating-Analyzer Ellipsometry", Optical Society of America, Vol. 5, No. 6 (1988), which identifies two types of errors, (ie. random and systematic).

A book by Azzam and Bashara titled "Ellipsometry and Polarized light" North-Holland, 1977 is disclosed and incorporated herein by reference for general theory.

As well, identified for authority regarding regression, is a book titled Numerical Recipes in "C", 1988, Cambridge University Press.

A need exists for a method of evaluating dependent variables which can be represented as a function of an independent variable in a mathematical function, based upon data which contains noise.

DISCLOSURE OF THE INVENTION

The disclosed invention is a method of reducing the effects of systematic and/or random noise during determination of, for instance, pseudo "n" and "k" and/or ellipsometric PSI and DELTA of a sample, comprising the steps of:

a) obtaining data corresponding to a dependent variable vs. an independent variable, said data having systematic or substantially random noise superimposed thereupon;

b) for at least one subset range of the independent variable, selecting and fitting a mathematical function to said data such that a plot of said mathematical function dependent variable vs. independent variable is positioned substantially centrally in said data which has systematic or substantially random noise superimposed therepon, over said independent variable subset range;

c) evaluating said mathematical function at least one independent variable value and accepting the result as the value of said dependent variable.

Said method can be repeated for at least one additional subset range of independent variable to provide additional results, and it is noted that while polynomials are generally useful, the Mathematical function need not be a polynomial or be of the same form in different subset ranges of data.

Where pseudo "In" and "k" and/or ellipsometric PSI and DELTA of a sample are the dependent variable, and multiple subset ranges of wavelengths as independent variable are investigated, the method of reducing the effect of noise during determination of the pseudo "n" and "k" and/or ellipsometric PSI and DELTA of the sample, can comprise the steps of:

a) obtaining data corresponding to pseudo "n" and "k", and/or ellipsometric PSI and DELTA vs. wavelength, said data having systematic or substantially random noise superimposed therepon;

b) for at least two subset ranges of wavelengths, via regression fitting some selected mathematical function to the data therewithin such that a plot of said function vs. wavelength is positioned substantially centrally in said data over each said wavelength subset range, the mathematical function utilized in the first subset of wavelengths not necessarily being the same as that utilized in the second subset of wavelengths;

c) evaluating said selected mathematical functions in each subset of wavelengths at least one wavelength therein, and accepting the resulting value as the value of said pseudo "n" and "k" and/or PSI and DELTA at said wavelengths.

Of course, said method could be applied to only one range of data and the recited method is exemplary only.

Said method can involve selecting mathematical functions and associated subset ranges of wavelengths applied such that when a square error reducing regression fitting of said mathematical function to obtained data corresponding to "n" and "k" and/or PSI and DELTA vs. wavelength, the sum of all the square of error of (data—mathematical function value at each wavelength over the subset range of wavelengths), is minimized, zero or within some selected acceptable deviation from zero. In fact, this is a very important consideration where introducing artifacts based on other than noise are to be avoided, while reducing the effects of noise.

An important step in the methodology, which justifies an investment of time to practice where for instance testing of production samples is contemplated, then is to seek optimum mathematical function/wavelength range combinations. For instance, it is generally expected that the same mathematical function will not be suitable for modeling an entire range of wavelengths, but rather different mathematical functions will apply in subsets of the entire wavelength range. (Note that the different mathematical functions can be of different, or the same or similar form, but with different dependent variable determining parameter values). A relevant method step involves selecting a mathematical function and wavelength range subset combination so that a square error best fit, with total summed square error over the wavelength subset range being minimized, zero or within an acceptable range near zero, are simultaneously achieved.

The step a obtaining of data corresponding to "n" and "k" and/or PSI and DELTA vs. wavelength, said data having systematic or substantially random noise superimposed therepon can comprise:

a) providing a material system investigation system comprising a source of a polychromatic beam of electromagnetic radiation, a polarizer means, a material system supporting Stage, an analyzer means and a detector means, said material system investigation system optionally comprising at least one compensator and/or aperture placed ahead of, and/or after said material system supporting stage, and a processor for performing calculations that evaluate detector means intensity output signal;

b) causing said source of a polychromatic beam of electromagnetic radiation to provide a beam of electromagnetic radiation and direct it to interact with a sample, (ie. by either reflection therefrom or transmission therethrough), which is placed on said material system supporting Stage after passing through said polarizer, and then proceed through said analyzer and into said detector means, which in turn produces data corresponding to intensity vs. wavelength which said processor utilizes to evaluate parameters in at least one mathematical function via an fitting routine.

It should be appreciated that data can be obtained as a function of angle-of-incidence instead of as a function of wavelength, and the same methodology still applies.

It is also noted that results at times improve when a larger diameter electromagnetic beam is used, (eg. as can effected by focusing said electromagnetic beam other than on the effective surface of the sample. Thus, an additional step can be providing means for determining the diameter of an electromagnetic beam where it impinges on a sample, (eg. lens and/or aperture), and adjusting said means to provide a desired beam diameter. This can considered to be a "defocusing" of the beam, which is functionally similar to focusing the beam before or after the location of a surface of the sample.

The disclosed invention will be better understood by reference to the Detailed Description in conjunction with the Drawings.

SUMMARY OF THE INVENTION it is therefore a purpose and/or objective of the disclosed invention to teach method of reducing the effect of systematic and/or random noise during determination of dependent variable values, (eg. pseudo "n" and "k" and/or ellipsometric PSI and DELTA or mathematical equivalent vs. wavelength and/or angle of incidence), involving selecting a mathematical function and an independent variable subset range combination so that a square error best fit with total summed square error over the independent variable subset range being minimized, zero or within an acceptable range near zero, are achieved.

Other purposes and/or objectives of the disclosed invention will become apparent upon a reading of the Specification and Claims.

DETAILED DESCRIPTION

Figure 1:
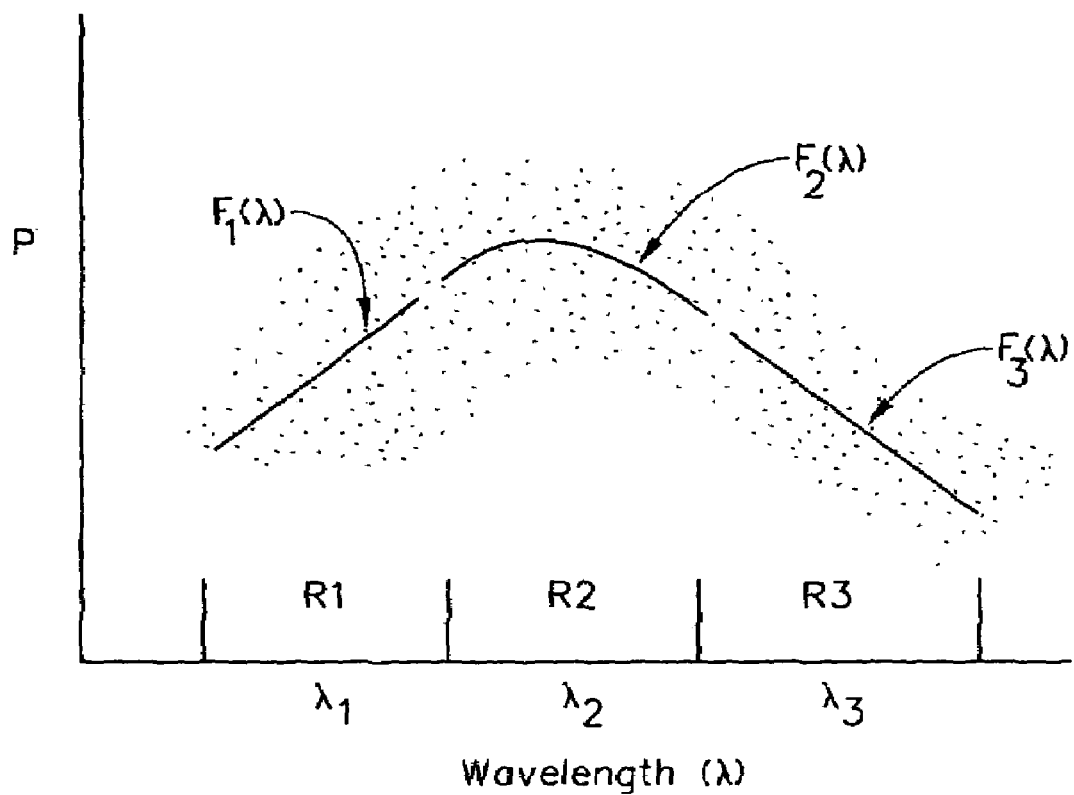
FIG. 1 shows a plot of Dependent Variable (P) vs. Independent Variable (WAVELENGTH).

FIG. 1 shows a plot of Dependent Variable (P) vs. Independent Variable (WAVELENGTH). Note that it is divided into three Wavelength subset ranges (R1), (R2) (R3), each of which can be fit by a separate mathematical function $F1(\lambda)$, $F2(\lambda)$ and $F3(\lambda)$. Note that $F1(\lambda)$ and $F3(\lambda)$ could be simple straight lines described by:

$$Y = mX + b;$$

and $F2(\lambda)$ an equation that provides a curve, perhaps a portion of a parabola:

$$(Y-k)^2 = 4a(X-h);$$

where k and h are vertex coordinates, and a is positive, or a polynomial:

$$Y = aX + bX^2 + cX^2 + \ldots$$

Any appropriate mathematical function can be applied.

Figure 2:
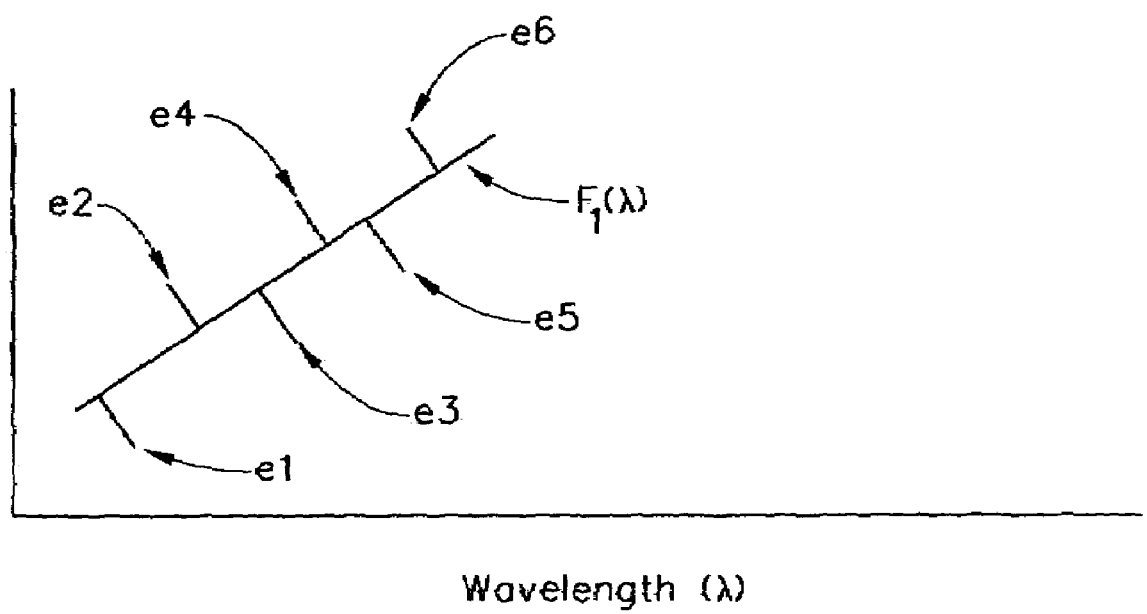
FIG. 2 shows that data points are offset from the locus of the plot of Equation F1( ), which Equation is typically fit to the data points by a regression procedure which reduces square error.

FIG. 2 shows that data points are offset from the locus of the plot of Equation $F1(\lambda)$, which Equation is typically fit to the data points by a regression procedure which reduces square error. The disclosed invention also identifies errors per se., e1, e2, e3, e4, e5 and e6, and a step in its method is to determine Mathematical Function and Wavelength Range combinations which result in the sum of $(e1^2 + e2^2 + e3^2 + e4^2 + e5^2 + e6^2$ being minimized, zero or within some acceptable range of deviation from zero in order to assure that the Mathematical Function is placed substantially centrally in said Data Points.

It is also to be understood that where PSI and DELTA or "n" and "k" are identified, mathematical equivalents are to be considered impliedly contained therewithin. For instance $<E_1>$ and $<E_2>$ are mathematical equivalents of "n" and "k".

It is to be understood that the terminology "Systematic" and "Substantially Random" Noise refer to noise which is, respectively, repeatable and non-repeatable. That is Systematic Noise appears the same each time data is obtained in a similar manner, whereas Substantially Random Noise is different each time data is obtained in a similar manner. The disclosed invention enables smoothing the effects of both types of noise during analysis.

It is also noted that while FIGS. 1 and 2 show "wavelength" as an independent variable, that could be replaced with "angle-of-incidence".

Figure 3A:
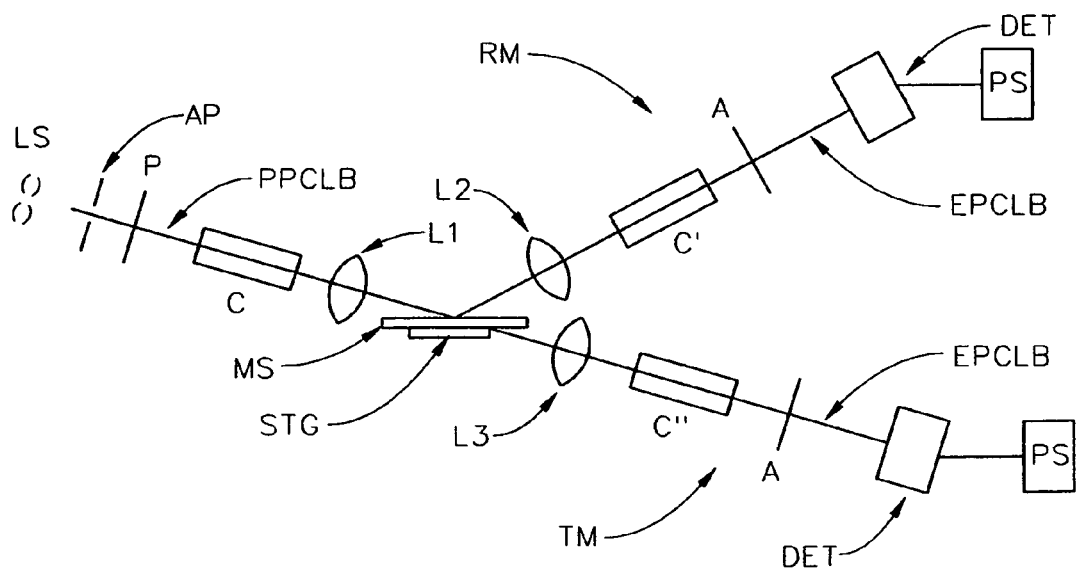
FIG. 3a shows the basic components of Reflectance and Transmission Mode Material System Investigation Systems.

FIG. 3a demonstrates a demonstrative, non-limiting, ellipsometer system which can be applied to practicing the disclosed invention. There is demonstrated a Material System Investigation System, (ie. a Spectroscopic Ellipsometer System), with provision to investigate a Material System (MS) in either a Reflection Mode (RM) or a Transmission Mode (TM). It is to be noted that said Material System investigation System is generally comprised of a Source of a Polychromatic Beam of Electromagnetic Radiation (LS), (ie. a Broadband electromagnetic radiation source), a Polarizer Means (P), a Material System, supporting Stage (STG), an Analyzer Means (A) and a Detector Elements (DE's) containing Photo Array Detector Means System (DET). Also note, however, that FIG. 3a shows Reflection Mode System Compensator(s) Means (C) and (C') and Transmission Mode System Compensator(s) Means (C) and (C") as present. It is to be understood that a Compensator Means can be placed ahead of, and/or after a Material System (MS) supporting Stage (STG) in either a Reflection Mode or Transmission Mode System. That is only Compensator Means (C) or (C') or both Compensator Means (C) and (C') can be present in a Reflection Mode System (RM), and only Compensator Means (C) or (C") or both Compensator Means (C) and (C") can be simultaneously present in the Transmission Mode System (TM). FIG. 3a also shows the presence of a Processor (PS) for performing calculations that evaluate a sample based on the Detector (DET) intensity output signal. Note that the indicated processor (PS) is not programmed with the same type of algorithm the processor in the Aspnes et al. patents is interpreted as containing. Also indicated are optional Apertures (AP), and Lenses (L1), (L2) and (L3).

It should be appreciated that the configuration in FIG. 3a could be operated as a Rotating Polarizer or Rotating Analyzer System. The disclosed Rotating Compensator Material System Investigation System, however, in the preferred operational mode, essentially fixes the Polarizer Means (P) and Analyzer Means (A) during Data Acquisition from a Material System (Sample) (MS) which is placed upon the Material System supporting Stage (STG), and causes at least one present Compensator Means ((C), and/or (C') or (C) and/or (C")), to Rotate during said Data Acquisition. This serves to effectively enter a continuously varying retardance between Orthogonal Components in a Polarization Beam of Electromagnetic Radiation exiting said Compensator Means which is caused to rotate. Where two (2) Compensator Means are present, one before (C) and one after ((C') or (C")) a Material System placed upon said Material System (MS) supporting Stage (STG), only one, or both said Compensator Means can be caused to Rotate in use. If both Compensator Means are caused to rotate, both can be rotated a the same rotation speed, or different rotation speeds can be utilized. It is noted that the J.A. Woollam CO. Rotating Compensator Ellipsometer uses a "Stepper Motor" to cause Compensator rotation, and a common signal synchronizes both the Compensator and Detector. An alternative technique is to use a signal derived from the motor to synchronize the detector means. It is further noted that fixing the Polarizer Means (P) and Analyzer Means (A) in use provides another benefit in that polarization state sensitivity to input and output optics during data acquisition is essentially non-existent. This allows use of Optic Fibers, Mirrors, Beam Splitters, Lenses etc. for input/output.

Figure 3B:
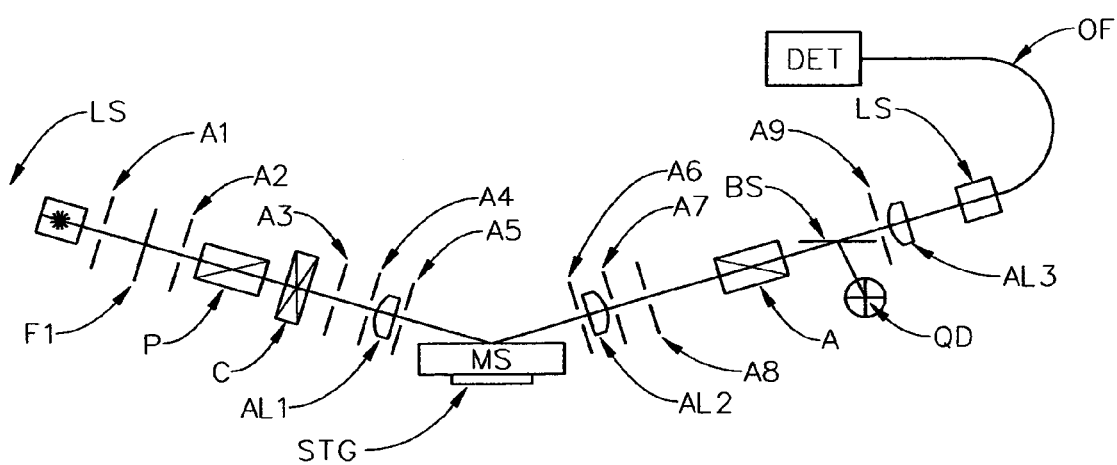
FIG. 3b shows the components of a Reflectance Mode Material System Investigation Systems which has five apertures in the pathway of an electromagnetic beam prior to a material system, and four thereafter.

For insight, FIG. 3b is included to show a preferred spectroscopic rotating compensator material system investigation system comprising a source (LS) of polychromatic beam of electromagnetic radiation, a first aperture (A1), a second aperture (A2), a fixed polarizer (P), a rotating compensator (C), a third aperture (A3), a forth aperture (A4), a first substantially achromatic lens (AL1), a fifth aperture (A5), a stage (STG) for supporting a material system, a sixth aperture (A6), a second substantially achromatic lens (AL2), a seventh aperture (A7), an eighth aperture (A8), a fixed analyzer (A), a ninth aperture (A9), a third substantially achromatic lens (AL3), an optical fiber (OF) and a detector means (DET) which contains a dispersive element and a multiplicity of detector means elements, there further being a UV filter (F1) present between said source (LS) of polychromatic beam of electromagnetic radiation and said stage (STG) for supporting a material system. When said spectroscopic rotating compensator material system investigation system is used to investigate a material system (MS) present on said stage (STG) for supporting a material system, said fixed analyzer (A) and fixed polarizer (P) are maintained essentially fixed in position and said rotating compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantially achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantially achromatic lens (AL2), seventh aperture (A7), eighth aperture (A8), fixed analyzer (A), ninth aperture (A9), third substantially achromatic lens (AL3), enter said optical fiber (OF) and therevia enter said detector means (DET).

It is also mentioned that in the following it will be generally assumed that a Material System (MS) under investigation by a Spectroscopic Rotating Compensator Material System Investigation System is positioned upon the Material System Supporting Stage (STG). This need not be the case, as is described in U.S. Pat. No. 5,706,087 wherein a Material System (Sample), (MS) can be positioned in a Magneto-Optic System which is physically too large to be supported by said Material System Supporting Stage (STG), or in an environmental control chamber. Further, especially where Ultraviolet range wavelengths are utilized, the system of FIG. 3a or 3b can be placed into an evacuated or purged, (eg. by nitrogen or argon), Chamber to the end that UV absorbing Oxygen and Water Vapor are not present therewithin. The entire FIG. 3a or 3b system can be so encompassed within a said Chamber, or only the Sample (MS) Stage portion thereof. The Chamber, where utilized, can be of multiple region construction.

Again, FIGS. 3a and 3b are included as demonstrative systems which can be applied to practice of the disclosed invention. The focus of the disclosed invention is, for at least one subset range of the independent variable, selecting and fitting a mathematical function to data such that a plot of said mathematical function vs. wavelength is positioned substantially centrally in said data which has systematic or substantially random noise superimposed therepon, over said independent variable subset range. The preferred approach to evaluating parameters in the mathematical function is regression.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of reducing the effect of noise during determination of at least one sample characterizing parameter, comprising the steps of:

a) providing a material system investigation system comprising a source of a polychromatic beam of electromagnetic radiation, a a material system supporting stage, and a detector means;

b) causing said source of a polychromatic beam of electromagnetic radiation to provide a beam of electromagnetic radiation and direct it to interact with a sample which is placed on said material system supporting stage, and then proceed into said detector means, which in turn produces data corresponding to intensity vs. wavelength as an independent variable, and therefrom determining sample characterizing parameter data vs. wavelength;

c) determining that an effective plot of said sample characterizing parameter data obtained in step b, as a function of wavelength, has systematic or substantially random noise superimposed thereupon;

d) for at least one subset range of wavelength selecting and fitting a mathematical function to said sample characterizing parameter data vs. wavelength such that a plot of said mathematical function vs. wavelength as independent variable is positioned substantially centrally in said dependent sample characterizing parameter data which has systematic or substantially random noise superimposed thereupon, over said independent variable subset range;

e) evaluating said mathematical function at at least one selected independent variable value and accepting the result as the value of said dependent sample characterizing parameter variable at that value of independent variable;

f) displaying at least some results determined in steps d and e;

the result being that the value of a dependent sample characterizing parameter at least one value of said at least one independent variable is determined, with the effect of noise on said result being decreased.

2. A method as in claim 1 in which said method is repeated for at least one additional subset range of independent variable to provide additional results.

3. A method of reducing the effect of noise during determination as in claim 2, wherein the mathematical functions in the two subset ranges of independent variable are characterized by a selection from the group consisting of:
   being of the same form;
   being of different form.

4. A method of reducing the effect of noise during determination as in claim 1, wherein the mathematical function is a polynomial.

5. A method of reducing the effect of noise during determination as in claim 4, wherein selection of a subset of independent variable and of the mathematical function are accomplished in combination and, for a selected mathematical function involves testing of various independent variable subset ranges such that when the mathematical function is fit to the data via a square error reducing routine, a simultaneous result is that the total summed square error is minimized, zero or within a selected range around zero.

6. A method of reducing the effect of noise during determination of at least one sample characterizing parameter, comprising the steps of:
   a) providing a material system investigation system comprising a source of a polychromatic beam of electromagnetic radiation, a a material system supporting stage, and a detector means;
   b) causing said source of a polychromatic beam of electromagnetic radiation to provide a beam of electromagnetic radiation and direct it to interact with a sample which is placed on said material system supporting stage, and then proceed into said detector means, which in turn produces data corresponding to intensity vs. angle-of-incidence as an independent variable, and therefrom determining sample characterizing parameter data vs. angle-of-incidence;
   c) determining that an effective plot of said sample characterizing parameter data obtained in step b, as a function of angle-of-incidence, has systematic or substantially random noise superimposed thereupon;
   d) for at least one subset range of angle-of-incidence selecting and fitting a mathematical function to said sample characterizing parameter data vs. angle-of-incidence such that a plot of said mathematical function vs. angle-of-incidence as independent variable is positioned substantially centrally in said dependent sample characterizing parameter data which has systematic or substantially random noise superimposed thereupon, over said independent variable subset range;
   e) evaluating said mathematical function at least one selected independent variable value and accepting the result as the value of said dependent sample characterizing parameter variable at that value of independent variable;
   f) displaying at least some results determined in steps d and e;
the result being that the value of a dependent sample characterizing parameter at least one value of said at least one independent variable is determined, with the effect of noise on said result being decreased.

7. A method as in claim 6 in which said method is repeated for at least one additional subset range of independent variable to provide additional results.

8. A method of reducing the effect of noise during determination as in claim 7, wherein the mathematical functions in the two subset ranges of independent variable are characterized by a selection from the group consisting of:
   being of the same form;
   being of different form.

9. A method of reducing the effect of noise during determination as in claim 6, wherein the mathematical function is a polynomial.

10. A method of reducing the effect of noise during determination as in claim 9, wherein selection of a subset of independent variable and of the mathematical function are accomplished in combination and, for a selected mathematical function involves testing of various independent variable subset ranges such that when the mathematical function is fit to the data via a square error reducing routine, a simultaneous result is that the total summed square error is minimized, zero or within a selected range around zero.

11. A method of reducing the effect of noise during determination of at least one sample characterizing parameter, comprising the steps of:
   a) providing a material system investigation system comprising a source of a polychromatic beam of electromagnetic radiation, a a material system supporting stage, and a detector means;
   b) causing said source of a polychromatic beam of electromagnetic radiation to provide a beam of electromagnetic radiation and direct it to interact with a sample which is placed on said material system supporting stage, and then proceed into said detector means, which in turn produces data corresponding to intensity vs. at least one independent variable selected from the group consisting of:
   angle-of-incidence; and
   wavelength;
and therefrom determining sample characterizing parameter data vs. said at least one selection from the group consisting of:
   angle-of-incidence; and
   wavelength;
   c) determining that an effective plot of said sample characterizing parameter data obtained in step b, as a function of said at least one selection from the group consisting of:
   angle-of-incidence; and
   wavelength;
has systematic or substantially random noise superimposed thereupon;
   d) for at least one subset range of said at least one independent variable selected from the group consisting of:
   wavelength; and
   angle-of-incidence;
selecting and fitting a mathematical function to said sample characterizing parameter data vs. a selection from said at least one independent variable selected from the group consisting of:
   wavelength; and
   angle-of-incidence;
such that a plot of said mathematical function vs. the independent variable is positioned substantially centrally in said dependent sample characterizing parameter data which has systematic or substantially random noise superimposed thereupon, over said independent variable subset range;
   e) evaluating said mathematical function at least one selected independent variable value and accepting the result as the value of said dependent sample characterizing parameter variable at that value of independent variable;

f) displaying at least some results determined in steps d and e;

the result being that the value of a dependent sample characterizing parameter at least one value of said at least one independent variable is determined, with the effect of noise on said result being decreased.

12. A method as in claim 11 in which said method is repeated for at least one additional subset range of independent variable to provide additional results.

13. A method of reducing the effect of noise during determination as in claim 12, wherein the mathematical functions in the two subset ranges of independent variable are characterized by a selection from the group consisting of:
being of the same form;
being of different form.

14. A method of reducing the effect of noise during determination as in claim 11, wherein the mathematical function is a polynomial.

15. A method of reducing the effect of noise during determination as in claim 11, wherein selection of a subset of independent variable and of the mathematical function are accomplished in combination and, for a selected mathematical function involves testing of various independent variable subset ranges such that when the mathematical function is fit to the data via a square error reducing routine, a simultaneous result is that the total summed square error is minimized, zero or within a selected range around zero.

16. A method of reducing the effect of noise as in claim 11, wherein the electromagnetic beam diameter at the effective surface of said sample is controlled.

17. A method of reducing the effect of noise during determination of at least one sample characterizing parameter value for a selection from the group consisting of:
pseudo "In";
pseudo "k";
PSI; and
DELTA;
comprising the steps of:
a) providing a material system investigation system comprising a source of a polychromatic beam of electromagnetic radiation, a polarizer means, a material system supporting stage, an analyzer means and a detector means, said material system investigation system optionally comprising at least one compensator and/or aperture placed at least one location selected from the group consisting of:
ahead of; and
after;
said material system supporting stage;
b) causing said source of a polychromatic beam of electromagnetic radiation to provide a beam of electromagnetic radiation and direct it to interact with a sample which is placed on said material system supporting stage after it passes through said polarizer, and then proceed through said analyzer and into said detector means, which in turn produces data corresponding to intensity vs. at least one independent variable selected from the group consisting of:
angle-of-incidence; and
wavelength;

and therefrom determining data corresponding to at least one sample characterizing parameter dependent variable selected from the group consisting of:
pseudo "n";
pseudo "k";
PSI; and
DELTA;
as a function of said at least one selected independent variable selected from the group consisting of:
angle-of-incidence; and
wavelength;
c) determining that an effective plot of the sample characterizing parameter dependent variable data selected from the group consisting of:
pseudo "n";
pseudo "k";
PSI; and
DELTA;
for said sample, determined from the data corresponding to intensity vs. said at least one selection from the group consisting of:
angle-of-incidence; and
wavelength;
as independent variable, obtained in step b, has systematic or substantially random noise superimposed thereupon;
d) for at least one subset range of said at least one independent variable selected from the group consisting of:
wavelength; and
angle-of-incidence;
selecting and fitting a mathematical function to said data corresponding to a selected sample characterizing parameter dependent variable selected from the group consisting of:
pseudo "n";
pseudo "k";
PSI; and
DELTA;
such that a plot of said mathematical function vs. the independent variable is positioned substantially centrally in said dependent sample characterizing parameter variable data which has systematic or substantially random noise superimposed therepon, over said independent variable subset range;
e) evaluating said mathematical function at least one selected independent variable value and accepting the result as the value of said dependent sample characterizing parameter variable at that value of independent variable;
f) displaying at least some results determined in steps d and e;
the result being that the value of a dependent sample characterizing parameter at least one value of said at least one independent variable is determined, with the effect of noise on said result being decreased.

18. A method as in claim 17 in which said method is repeated for at least one additional subset range of independent variable to provide additional results.

19. A method of reducing the effect of noise during determination as in claim 18, wherein the mathematical functions in the two subset ranges of independent variable are characterized by a selection from the group consisting of:
being of the same form;
being of different form.

20. A method of reducing the effect of noise during determination as in claim 17, wherein the mathematical function is a polynomial.

21. A method of reducing the effect of noise during determination as in claim 17, wherein selection of a subset of independent variable and of the mathematical function are accomplished in combination and, for a selected mathematical function involves testing of various independent variable subset ranges such that when the mathematical function is fit to the data via a square error reducing routine, a simultaneous result is that the total summed square error is minimized, zero or within a selected range around zero.

22. A method of reducing the effect of noise as in claim 17, wherein the electromagnetic beam diameter at the effective surface of said sample is controlled.

* * * * *